United States Patent [19]

Fowles

[11] Patent Number: 5,167,642
[45] Date of Patent: Dec. 1, 1992

[54] SHEATH FOR A BLUNT CANNULA

[75] Inventor: Thomas A. Fowles, McHenry, Ill.

[73] Assignee: Baxter International Inc., Deerfield, Ill.

[21] Appl. No.: 573,529

[22] Filed: Aug. 27, 1990

[51] Int. Cl.$^5$ .............................................. A61M 5/00
[52] U.S. Cl. ...................................... 604/263; 604/86; 604/88; 604/244; 604/411
[58] Field of Search .............. 604/83, 87, 88, 192, 604/198–200, 244, 263, 411, 413, 414; 128/764

[56] References Cited

U.S. PATENT DOCUMENTS

| | | |
|---|---|---|
| 3,734,080 | 5/1973 | Petterson et al. ................. 128/764 |
| 3,886,930 | 6/1975 | Ryan ................................. 128/764 |
| 4,197,848 | 4/1980 | Garrett et al. ..................... 604/19 |
| 4,200,100 | 4/1980 | Willis ................................ 604/414 |
| 4,416,290 | 11/1983 | Lutkowski ....................... 128/764 |
| 4,449,539 | 5/1984 | Sarstedt ............................ 128/764 |
| 4,564,054 | 1/1986 | Gustavsson ....................... 604/198 |
| 4,804,366 | 2/1989 | Zdeb et al. ......................... 604/85 |
| 4,846,809 | 7/1989 | Sims .................................. 604/198 |
| 4,850,978 | 7/1989 | Dudar et al. ...................... 604/201 |
| 4,998,921 | 3/1991 | Vickroy et al. ................... 604/192 |

OTHER PUBLICATIONS

Webster's II New Riverside University Dictionary, 1984, p. 169.

Primary Examiner—John D. Yasko
Assistant Examiner—Anthony Gutowski
Attorney, Agent, or Firm—Paul E. Schaafsma; Amy L. H. Rockwell; Paul C. Flattery

[57] ABSTRACT

The present invention provides a sheath for at least removably covering the blunt end of the cannula. The sheath allows the cannula to be presterilized and utilized without subsequent sterilization. The sheath comprises a body member defining an interior for receiving at least a portion of the blunt cannula, the body member including a first end and a second end, the second end having an opening for receiving at least a portion of the cannula. The first end including a wall member so constructed and arranged as to rip upon the exertion of a sufficient perpendicular force by an end of the blunt cannula. The body also includes side walls extending between the first and second end, the side walls are so constructed and arranged so as to slide back along the cannula toward the second end upon the tearing of the first end by the cannula and the application of a sufficient force upon the side walls.

31 Claims, 3 Drawing Sheets

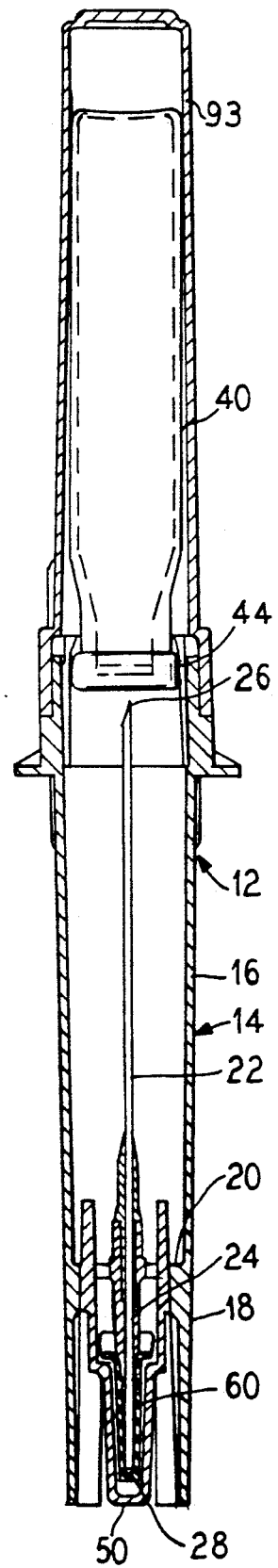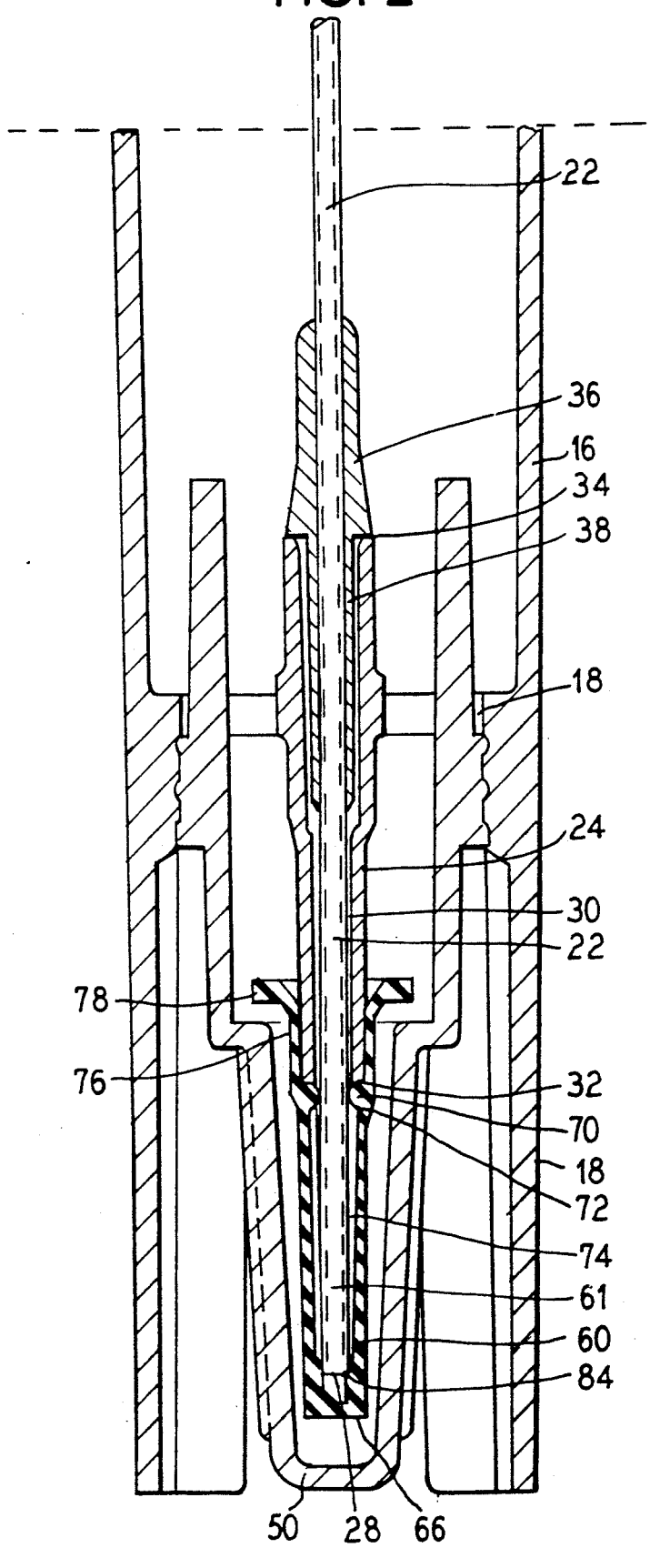

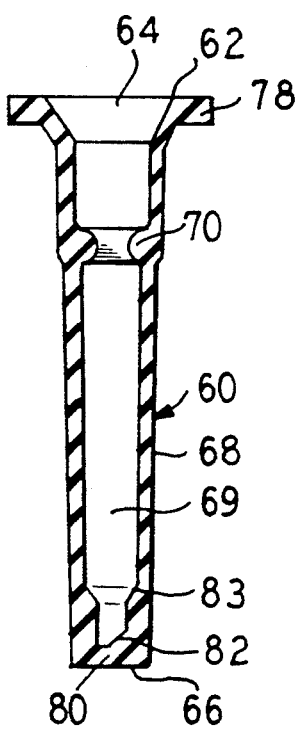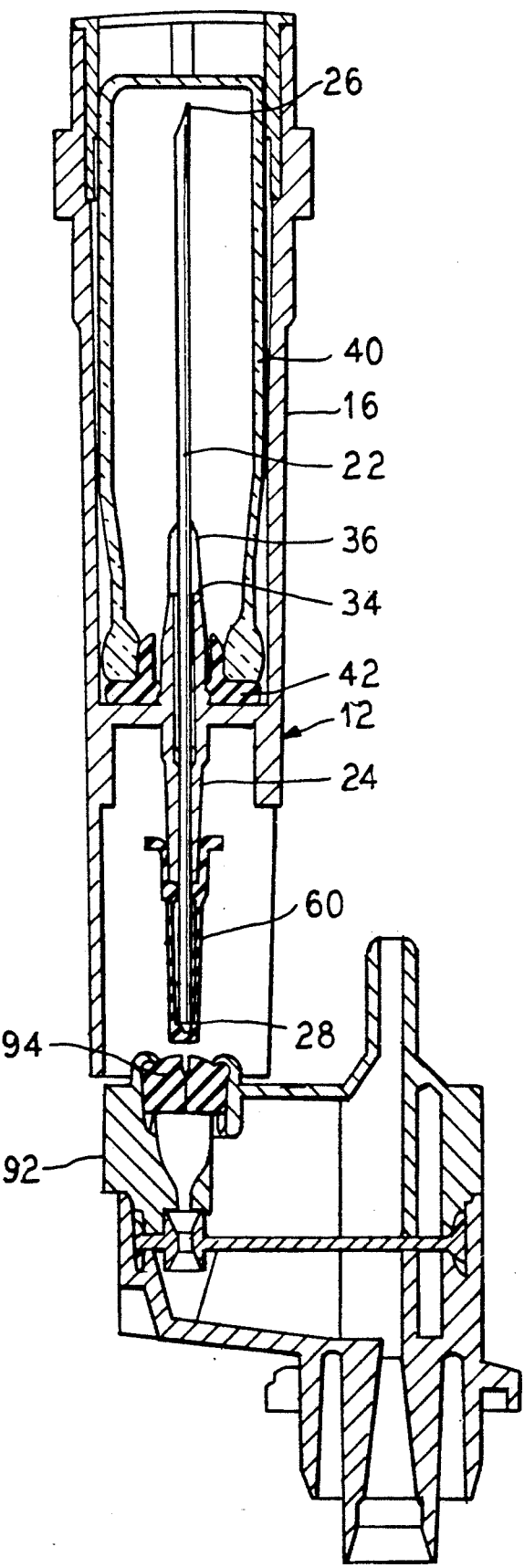

SHEATH FOR A BLUNT CANNULA

BACKGROUND OF THE INVENTION

The present invention relates generally to the delivery of a beneficial agent to a patient or into a system for later delivery to a patient. More specifically, the present invention relates to a sheath for covering a blunt end of a cannula.

Pointed cannulas, for use with injection sites, have been known for use in the medical arena. Such cannulas can be utilized to access a medicament contained within a container or to create a fluid flow path within a housing. An example of an injection site usable with a piercing cannula is disclosed in U.S. Pat. No. 4,412,573.

Within a housing, to create a fluid flow path, a pointed cannula is utilized that is forced through a septum to create a flow path within the housing. Injection sites, however, which are utilized on a repetitive basis can be damaged by repetitive piercing by a sharp cannula. This damage, known as coring or laceration, can result in a subsequent leakage within the housing.

Furthermore, the use of a pointed cannula has the further disadvantage that it can detrimentally affect the personnel using the pointed cannulas. For example, recently there has been much concern over the transfer of infectious agents and disease states, for example, acquired immune deficiency syndrome, by personnel piercing themselves with pointed cannulas. Further, many medications that are utilized can be dangerous if one is repeatedly exposed to such medicine by being pierced by the pointed cannula, e.g., chemotherapy drugs.

Accordingly, recently, blunt cannulas have been developed for utilization with specific injection sites that are designed to receive such cannulas. An example of such a site is set forth in U.S. Pat. No. 4,197,848. That patent discloses an injection site having a relatively low pressure device having a relatively thin, molded sealing member. The sealing member has an opening therethrough. The blunt cannula can be forced through the sealing member placing the cannula into fluid flow communication with a fluid flow pathway in the injection site.

Blunt cannulas have the advantage that the blunt end of the cannula cannot accidentally pierce the skin of the medical personnel. Accordingly, even if one accidentally contacts the cannula, the cannula will not pierce his skin.

For use with blunt cannulas, preslit injection sites have been developed. An example of these preslit injection sites includes U.S. patent application Ser. No. 07/147,414, assigned to the assignee of the instant patent application. The preslit injection site allows the blunt end of the cannula to be received within the injection site, establishing fluid communication.

For many applications, drugs may be mixed with a diluent before being delivered, for example, intravenously, to a patient. The diluent may be, for example, a dextrose solution, a saline solution, or even water. To this end, many such drugs are supplied in powder form and packaged in glass vials or ampules. Other drugs, such as some chemotherapy drugs, are packaged in glass vials or ampules in a liquid state.

Powder drugs may be reconstituted by utilizing a syringe to inject liquid into a vial for mixing; the syringe eventually withdrawing the mixed solution from the vial. When a drug must be diluted before delivery to a patient, the drug is often injected into a container of diluent after it is reconstituted; the container can be connected to an administration set for delivery to the patient.

There are a variety of examples of drug delivery systems. An example of such a system is disclosed in U.S. Pat. No. 4,850,978. The system includes a cartridge for introducing a beneficial agent into a fluid conduit for delivery of the agent to a patient. The cartridge includes a rigid hollow tube and an agent-containing chamber slidably mounted at least partially within the hollow tube. In a first, pre-use position, the chamber extends farther from the hollow tube than it does in a second position. A cannula is mounted to the hollow tube extending opposite the chamber. When the chamber is in the second position, the cannula pierces the closure means creating a fluid flow path.

U.S. Pat. No. 4,804,366 also discloses a drug delivery system including an adapter having an improved flow path means providing both an inlet and an outlet to the agent-containing chamber of a cartridge. The cartridge and adapter permit a single opening through the injection sites at opposite ends of the flow path means, while still permitting simultaneous flow both into and out of the chamber. An adapter and a cartridge is provided, including a rigid cannula with an inlet and an outlet and a shell substantially coaxial with and spaced from the cannula intermediate of the cannula inlet and the cannula outlet, so that the shell of the cannula define a channel therebetween. Both the cannula inlet and the cannula outlet are adaptable to form a single piercing opening in a resilient injection site associated with the receptacle of the delivery system. Both the channel outlet and cannula inlet are adapted to form a single piercing opening in a resilient injection site associated with the cartridge.

It is known to provide a removable cover for surrounding a first end of the cannula that is coupled to a set. The cover is removed prior to connecting the system to an injection site of a set. Typically, the cover is removed after the cannula inlet has pierced the cartridge chamber. Because the cover must be removed prior to connecting the system to a set, and typically, after the cannula inlet has pierced the cartridge chamber, there may be concerns vis-a-vis sterility and leakage of product through the outlet end of the cannula as well as the channel inlet.

SUMMARY OF THE INVENTION

The present invention provides a means of maintaining a seal at a blunt end of a cannula while allowing the cannula to be received within an injection site. To this end, a sheath is provided for at least removably covering the blunt end of the cannula. The sheath allows the cannula to be presterilized and utilized without subsequent sterilization.

In an embodiment, the sheath provides a means of maintaining a seal at the blunt end of an inline cartridge needle and at the interface of the needle and cartridge, i.e., provides a seal at the distal end of both lumen paths in the inline device. The seal remains intact and prevents leakage of drug/solution before and during vial activation and attachment to an inline IV set. The sheath of the present invention does not interfere with the docking of the injection site. The sheath is designed to rip, and not core, as the blunt cannula is urged into an injection site.

The sheath comprises a body member defining an interior for receiving at least a portion of the blunt cannula, the body member including a first end and a second end, the second end having an opening for receiving at least a portion of the cannula. The first end including a wall member so constructed and arranged as to rip upon the exertion of a sufficient perpendicular force by an end of the blunt cannula. The body also includes side walls extending between the first and second end, the side walls are so constructed and arranged so as to slide back along the cannula toward the second end upon the tearing of the first end by the cannula and the application of a sufficient force upon the side walls.

In an embodiment, the body member includes at least one seal point located on an interior surface of the body member. The seal point circumscribes a portion of the outer surface of the cannula when the cannula is received within the interior of the sheath.

In an embodiment, the wall of the first end includes on an inner surface a bevelled portion.

In an embodiment, the wall of the first end includes a cross-sectional thickness greater than the cross-sectional thickness of a majority portion of the side walls.

In a further embodiment, a sheath for covering a blunt end of a cannula designed to enter an injection site having a body and a preslit opening is provided. The sheath includes a body defining an interior for receiving at least a portion of the cannula, the body having a first end and a second end. The second end having an opening for receiving at least a portion of the cannula, the first end including an end wall including means for causing the end wall to rip as the sheath and cannula are urged against the injection site allowing the blunt end of the cannula to enter the preslit opening. The body includes side walls, located between the first and second ends, that are so constructed and arranged so as to slide along the cannula toward the second end as the cannula is received within the preslit opening of the injection site.

In another embodiment, a cartridge for introducing a beneficial agent into a fluid conduit for delivery of the beneficial agent is provided comprising a hollow tube and a chamber having a beneficial agent therein. The chamber is mounted adjacent a first end of the hollow tube and is slidably mounted at least partially within the hollow tube from a first position to a second position; in the first position, the chamber extends a greater distance from the hollow tube than in the second position. A cannula is mounted within the hollow tube and includes a blunt end and a sheath for covering at least the blunt end of the cannula. The sheath includes a body defining an interior for receiving the blunt end of the cannula, the body including a first end including a wall member so constructed and arranged as to rip upon the exertion of a sufficient perpendicular force by an end of the blunt cannula, and a second end having an opening. The body includes side walls extending between the first and second end, the side walls are so constructed and arranged so as to slide back along the cannula toward the second end upon the tearing of the first end by the cannula and the application of a sufficient force upon the side walls.

A method for partially enclosing a cannula including a blunt end and allowing subsequent fluid communication between the cannula and an injection site is also provided. The method comprises the steps of: providing a sheath including an interior for receiving at least a portion of the blunt end of the cannula, the sheath including an end wall and side walls; urging the end wall of sheath and blunt end of the cannula against the injection site; causing the end wall to rip allowing the blunt end of the cannula to enter the injection site; urging the blunt end of the cannula into the injection site; and causing the side walls to roll up away from the end wall as the cannula is received within the injection site.

Additional features and advantages of the present invention are described in, and will be apparent from, the detailed description of the presently preferred embodiments and from the drawings.

BRIEF DESCRIPTION OF THE DRAWINGS

FIG. 1 illustrates a cross-sectional perspective view of an inline device including the cannula sheath of the present invention.

FIG. 2 illustrates an enlarged cross-sectional view of the device of FIG. 1 showing the blunt end of the cannula and sheath of the present invention.

FIG. 3 illustrates a cross-sectional perspective view of an embodiment of the sheath of the present invention.

FIG. 4 illustrates a cross-sectional perspective view of an inline device, including the cannula sheath of the present invention prior to docking with an injection site of a set.

DETAILED DESCRIPTION OF THE PRESENTLY PREFERRED EMBODIMENTS

Figure 6:
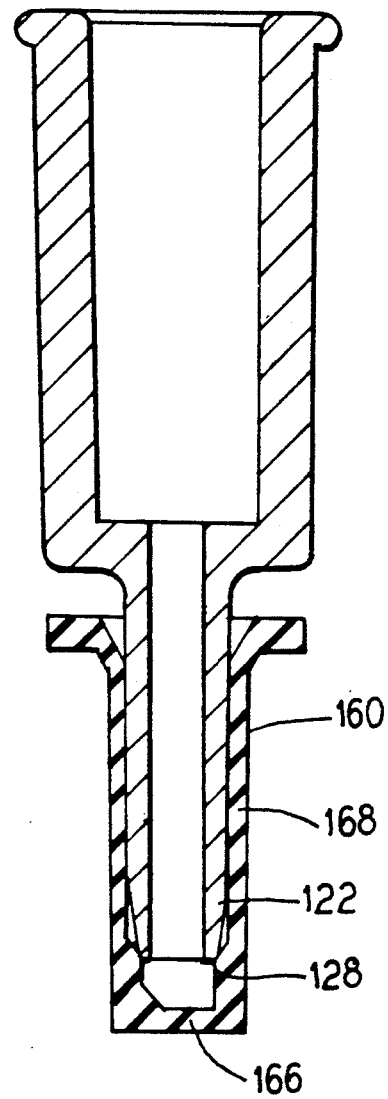
FIG. 6 illustrates a cross-sectional view of another embodiment of the sheath of the present invention.

The present invention provides a sheath for removably covering a blunt end of a cannula that is to be received within an injection site. Although the present invention is set forth by way of example in an embodiment of the patent application for use in a drug delivery system including an inline device for docking with an IV set, of course, the instant invention can be used in other devices incorporating a blunt cannula that is inserted within an injection site. An example of such a device is illustrated in FIG. 6.

Referring now to FIG. 1, there is illustrated an inline device, or cartridge, that is to be coupled to an IV set. The cartridge can be substantially similar to that disclosed in U.S. Pat. No. 4,804,366 that is incorporated herein by reference. Briefly, the cartridge 12 includes an adapter 14 having a rigid hollow cylinder or tube means 16 and a keyway wall 18, with the keyway wall 18 being part of the tube 16. A plate 20 is mounted across the tube 14 and defines the starting point for the keyway wall 18.

A cannula 22 extends through the plate 20. A generally cylindrical shell 24 extends from both sides of the plate 20. The hollow tube 16, the plate 20, and the shell 24 may all be formed as a single piece of the same material such as a plastic.

The shell 24 is spaced from the cannula 22 with the shell 24 encompassing the cannula 22 but being shorter than either end of the cannula 22. The cannula 22 includes an inlet 26 and an outlet 28. The inlet 26 preferably is pointed to facilitate piercing. The outlet 28 is preferably blunt and, as discussed in more detail hereinafter, is covered by the sheath 60 of the instant invention.

The shell 24 is intermediate of the cannula inlet and outlet 26 and 28, respectively. The cannula 22 and the shell 24 define a channel 30 therebetween. In a preferred embodiment, the periphery of the cannula 22 is circular along its length. Similarly, the internal surface of the shell 24 is preferably arcuate and preferably circular along its length.

The channel 30 includes a channel 32 inlet defined between the shell 24 and the cannula 22, short of the cannula outlet 28. Similarly, the channel 30 includes a channel outlet 34 defined by the shell 24 and the cannula 22, short of the cannula inlet 26.

A preferably plastic cannula holder 36 is secured to the cannula 22. The cannula holder 36 grips the cannula 22. Extension means 38 extend between the cannula holder 36 and the shell 24, across the channel 30, thereby securing the cannula 22 relative to the shell 26. In the illustrated embodiment, the extension means 38 is part of the holder 36.

The cannula 22 is secured to the shell 24 while still maintaining an open flow path through the channel inlet 32, the channel 30, and the channel outlet 34. Thus, a very small flow path is created outside a single cannula 22, with precision.

The cartridge 12 further includes a tubular chamber 40 containing a beneficial agent such as a dry powdered drug, although the agent may also be a liquid. In an embodiment, the tubular chamber 40 is a glass vial. A pierceable stopper 42 or other closure means closes the tubular chamber 40.

The shell 24, along with the channel outlet 34 and the cannula inlet 26, are designed to pierce the pierceable stopper 42 or other injection site/closure means to the chamber 40 having the beneficial agent therein. Similarly, as discussed in more detail hereinafter, the shell 24 along with the defined channel inlet 32, together with the cannula outlet 28, are designed to pierce the injection site in a receptacle.

The pierceable stopper 42 is mounted within the mouth 44 of the tubular chamber 40. The rubber stopper 42 may be secured within the tubular chamber 40 by means of a metal band about the periphery of the mouth and the rubber stopper, in a known manner for securing of a stopper in a standard drug vial. The tubular chamber 40 is slidably mounted within the rigid cylinder such that the rubber stopper 42 faces the plate 20. In place of the pierceable stopper 42, other pierceable closure means may be provided.

When the chamber 40 is in a first position, the rubber stopper 42 has not been pierced by either the shell 24 or the cannula inlet 26. The pierceable stopper 42 remains spaced from the cannula 22 when the cartridge 40 is in the first position.

The cannula 22 and the shell 24 comprise flow path means, which is part of the adapter means, which itself may be part of the cartridge. The hollow tube 16 is mounted about the chamber 40 and the adapter facilitates mounting the cartridge upon the receptacle. The adapter 14 slides relative to chamber 40. Stated differently, the chamber 40 and the adapter 14 are selectively slidable relative to each other.

The cartridge 12, in the embodiment illustrated, also includes a cartridge-removable cannula cover 50 removably secured within the base plate 20. The cartridge-removable cannula cover 50 has as its principal purpose preventing the connection of the cartridge 12 to the receptacle without first piercing the stopper 42 with the cannula 22 and shell 24. The cannula cover 50 ensures that the chamber 40 must be moved from the first position to the second position before the cartridge 40 can be mounted upon the receptacle.

As illustrated, pursuant to the present invention, a sheath 60 for covering the blunt end 28 of the cannula 22 is provided. The sheath 60 is designed to cover at least a portion 61 of the blunt end 28 of the cannula 22.

Referring now to FIG. 3, the sheath 60 includes a first end 62 having an opening 64 and a second end 66 that is closed. Extending between the first and second ends 62 and 66, respectively, are side walls 68. As discussed in more detail hereinafter, the sheath 60 is designed to rip, not core upon the exertion of a sufficient force by a blunt end 28 of the cannula 22 on the second end 66 of the sheath.

As illustrated, the interior 69 of the sheath 60 includes at least one rib 70 or shoulder that circumscribes, when the sheath 60 is located over the cannula 22, a portion of the cannula 22. This rib 70 creates a seal point 72 at an end of the shell 24 that defines the inlet opening 32 of the channel 30 defined by the shell 24 and the cannula 22. This seal 72 prevents fluid communication from the channel 30 and a lower portion 74 of the sheath 60.

An upper wall portion 76 of the sheath 60, located between the first end 64 and the rib 70 is so constructed and arranged to receive the lower portion of the shell 24 that defines the channel inlet 32 in a fluid sealingly tight arrangement. The upper wall portion 76 also includes angular walls 78 that circumscribe the sheath 60 and define the first end 62 opening 64 of the sheath.

Located at the second end 66, or closed end, of the sheath 60, the sheath includes end walls 80 having an increased thickness. The end walls 80 have a cross-sectional thickness that is greater than that the cross-sectional thickness of a majority portion of the side walls 68 of the sheath 60. The end walls also define a bevelled portion 82 that contacts, or is in juxtaposition, to the blunt end 28 of the cannula 22. This construction of the end walls 80 provides one of the advantages of the sheath 60 in that the sheath will rip, not core, upon the exertion of a sufficient force by the blunt end of the cannula against the end walls. This allows the blunt end 28 of the cannula 22 to be received within an injection site without first having to manually remove the sheath 60.

A tapered portion 83 provides a seal point 84 at an end of the cannula 22 preventing the flow of material from the cannula 22 into a lower portion 74 of the sheath 60.

As illustrated, the sheath 60 provides a covering that maintains the sterility of the blunt end 28 of the cannula 22, as well as an end of the shell 24. Furthermore, the sheath 60 prevents fluid or powdered drug from flowing through either the channel 30 or the cannula 22 and into the environment located outside of the sheath. Therefore, even though the cannula cover 50 has been removed, and the inlet end 26 of the cannula 22 received within the stopper 42 of the vial 40, fluid flow through the channel 30 and the cannula 22 is prevented by the sheath 60.

As previously stated, the cartridge 12 is designed to be connected to an administration set for delivering the beneficial agent in the vial to a patient. To this end, the cartridge including the beneficial agent is mounted upon the receptacle 92.

Prior to docking the cartridge 12 on the receptacle 92, the cartridge is activated. To activate the cartridge, a shrink wrap band (not shown) is torn away. The operator removes a protective cover 93 from the remainder of the cartridge 12.

The operator then grasps the rigid tube 16 and pushes down on the top of the chamber 40 with the thumb, thereby slidably moving the cartridge chamber 40 within the hollow tube 16. In this one action, first the cannula inlet 26 and then the shell 24 pierce the pierceable stopper 42. In the preferred construction illustrated in the drawings, after the cannula inlet 26 pierces the stopper 42, the cannula holder 36 pierces the stopper, followed by the shell 24, with the shell and the cannula holder defining the channel outlet 34, which is now disposed slightly within the chamber 40. In the same motion, the chamber 40 continues to be urged into the hollow tube 16 until it causes the cannula cover 50 to fall out of the cartridge 12.

With the cartridge chamber 40 now in the second position, the cartridge 12 is mounted upon the receptacle as illustrated in FIG. 4. FIG. 4 illustrates the cartridge 12 prior to the insertion of the outlet end 28 of the cannula 22 into the injection site 94 of the receptacle 92. Preferably, the injection site 94 is a preslit injection site. As illustrated, the sheath 60 still remains on the cannula 22 preventing the agent contained within the chamber 40 from leaking out and also maintains sterility of the covered portion of the cannula.

Figure 5:
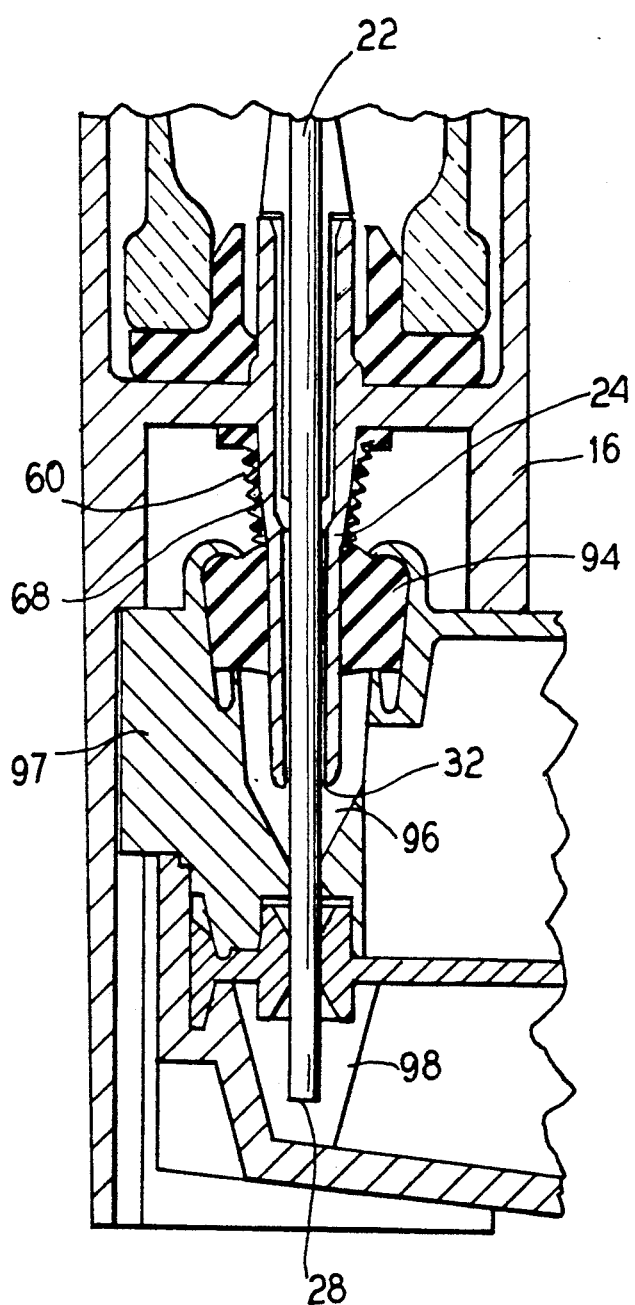
FIG. 5 illustrates a cross-sectional perspective view of the inline set after docking with the injection site of the set.

FIG. 5 illustrates the adapter after the blunt end 28 of the cannula 22 has been inserted through, with a portion of the shell 24, the preslit injection site 94. As illustrated, when the blunt end 26 of the cannula 22 is urged against the second end 66 of the sheath 60, the sheath rips and folds back along the cannula and the shell in an accordion fashion. This allows the blunt end 28 of the cannula 22 and shell 24 to enter the injection site 94 but prevents the sheath 60 from entering the injection site. Accordingly, fluid communication is established between the channel 30 and a portion 96 of the administration port and the cannula 22 and an internal portion 98 of the administration port.

Thus, the sheath 60 of the present invention allows one to maintain the aseptics of the blunt end 26 of the cannula 22 and a corresponding portion of the shell 24 while still allowing, without manual removal of the sheath, the adapter to dock with the injection site 92. Further, the sheath 60 prevents fluid flow or powder, depending on the drug and its method of administration, from flowing out of either the channel 30 defined by the shell 24 and cannula 22 or the cannula 22 itself prior to insertion of the blunt end 26 of the cannula 22 into the injection site 94.

Preferably, the sheath 60 is constructed from a material that will allow ETO sterilization of the cannula 22 and corresponding shell 24. In a preferred embodiment, the sheath 60 is constructed from silicon rubber.

As illustrated, preferably the second end 66 of the sheath 60 is flat. A flat end portion 66 of the sheath 60 helps in the shearing action causing the end to rip, not core, upon the exertion of a sufficient force by the blunt end of the cannula 22. Additionally, this flat design assists in allowing the sheath to fold back along the cannula in an accordion fashion.

Referring now to FIG. 6, a further embodiment of the sheath 160 of the present invention is illustrated. As illustrated, the sheath 160 is designed for use with a blunt cannula 122 that is received within, preferably, a preslit injection site. The sheath 160 provides a cover for a portion of the cannula 122 that maintains the sterility of the cannula prior to its insertion into the injection site.

The sheath 160, as in the previous embodiment, includes end wall 166 that is designed to rip, not core, upon the exertion of a sufficient force by the blunt end 128 of the cannula. After the second end 166 rips, the side walls, as in the previous embodiment, fold back as the cannula 122 is received in the injection site. If desired, the side walls 168 of the sheath 160 can be constructed so that they return and cover the cannula 122 as the cannula is removed from the injection site 192.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A blunt cannula and sheath for removably covering a blunt end of the cannula comprising:

a cannula having a blunt end; and a sheath including a body member defining an interior for receiving at least a portion of the blunt end of the cannula, the body member including a first end and a second end, the second end having an opening for receiving at least a portion of the cannula, the first end including a wall member that includes on an inner surface thereof a bevelled portion so constructed and arranged as to rip upon the exertion of a sufficient perpendicular force by the blunt end of the cannula, and the body includes side walls extending between the first and second end, the side walls are so constructed and arranged so as to slide back along the cannula toward the second end upon the tearing of the first end by the cannula and the application of a sufficient force upon the side walls.

2. A cannula that is designed to enter an injection site having a preslit opening including a sheath for covering a blunt end of the cannula comprising:

a cannula having a blunt end; and the sheath including a body defining an interior for receiving at least a portion of the cannula, the body having a first end and a second end, the second end having an opening for receiving at least a portion of the cannula, the first end including an end wall including an inner bevelled portion for causing the end wall to rip as the sheath and cannula are urged against the injection site allowing the blunt end of the cannula to enter the preslit opening, and the body including side walls located between the first and second ends, the side walls being so constructed and arranged so as to slide along the cannula toward the second end as the cannula is received within the preslit opening of the injection site.

3. A sheath for removably covering a blunt end of a cannula comprising:

a body member defining an interior for receiving at least a portion of a blunt end of a cannula, the body member including a first end and a second end, the second end having an opening for receiving at least a portion of the cannula, the first end including a wall member that includes on an inner surface thereof a bevelled portion, the bevelled portion having a cross-sectional thickness that varies along a length thereof and being so constructed and arranged as to rip upon the exertion of a sufficient perpendicular force by the blunt end of the cannula, and the body includes side walls extending between the first and second end, the side walls are so constructed and arranged so as to slide back along the cannula toward the second end upon the tearing of the first end by the cannula and the application of a sufficient force upon the side walls.

4. The sheath of claim 3 wherein the body member includes at least one seal point located on an inner surface of the body member, the seal point circumscribing a portion of the outer surface of the cannula when the cannula is received within the interior of the sheath.

5. The sheath of claim 3 wherein the body member includes at least two seal points located on an inner surface of the body member, one of the seal points circumscribing a portion of the outer surface of the cannula located near the blunt end of the cannula and the other seal point circumscribing another portion of the outer surface of the cannula when the cannula is received within the interior of the sheath.

6. A sheath for removably covering a blunt end of a cannula comprising:
   a body member defining an interior for receiving at least a portion of a blunt end of a cannula, the body member including a first end and a second end, the second end having an opening for receiving at least a portion of the cannula, the first end including a wall member that includes on an inner surface thereof a bevelled portion so constructed and arranged as to rip upon the exertion of a sufficient perpendicular force by the blunt end of the cannula, and the body includes side walls extending between the first and second end, the side walls are so constructed and arranged so as to slide back along the cannula toward the second end upon the tearing of the first end by the cannula and the application of a sufficient force upon the side walls, the wall of the first end has a cross-sectional thickness greater than the cross-sectional thickness of a majority portion of the side walls.

7. The sheath of claim 3 wherein the body member is constructed from silicone rubber.

8. The sheath of claim 3 wherein the body member is ETO gas transmissive.

9. The sheath of claim 3 wherein the body includes on an inner surface at least one rib for sealing at least one portion of the interior from another portion of the interior when a cannula is received within the sheath.

10. The sheath of claim 3 wherein the second end includes an annular portion that extends outwardly substantially perpendicular to the side walls.

11. The sheath of claim 3 wherein an outer surface of the first end is substantially flat.

12. A sheath for covering a blunt end of a cannula, the cannula being designed to enter an injection site having a preslit opening comprising:
   a body defining an interior for receiving at least a portion of the cannula, the body having a first end and a second end;
   the second end having an opening for receiving at least a portion of the cannula, the first end including an end wall having a cross-sectional thickness that varies at least along portions of a length thereof including an inner bevelled portion, the bevelled portion having a cross-sectional thickness that varies along a length thereof, for causing the end wall to rip as the sheath and cannula are urged against the injection site allowing the blunt end of the cannula to enter the preslit opening, and the body including side walls located between the first and second ends, the side walls being so constructed and arranged so as to slide along the cannula toward the second end as the cannula is received within the preslit opening of the injection site.

13. The sheath of claim 12 wherein the side walls are so constructed and arranged to return and cover at least a portion of the blunt end of the cannula when the cannula is removed from the injection site.

14. The sheath of claim 12 including at least one rib member circumscribing an inner surface of the body and contacting a portion of the cannula when the cannula is received within the interior.

15. A sheath for covering a blunt end of a cannula, the cannula being designed to enter an injection site having a preslit opening comprising:
   a body defining an interior for receiving at least a portion of the cannula, the body having a first end and a second end;
   the second end having an opening for receiving at least a portion of the cannula, the first end including an end wall including an inner bevelled portion for causing the end wall to rip as the sheath and cannula are urged against the injection site allowing the blunt end of the cannula to enter the preslit opening, and the body including side walls located between the first and second ends, the side walls being so constructed and arranged so as to slide along the cannula toward the second end as the cannula is received within the preslit opening of the injection site, the wall of the first end has a cross-sectional thickness greater than the cross-sectional thickness of a majority portion of the side walls.

16. The sheath of claim 12 wherein the second end includes an annular portion that extends outwardly substantially perpendicular to the side walls.

17. The sheath of claim 12 wherein the body includes on an inner surface at least one rib for sealing at least one portion of the interior from another portion of the interior when a cannula is received within the chamber.

18. The sheath of claim 12 wherein an outer surface of the sheath defined by the end wall is substantially flat.

19. A cartridge for introducing a beneficial agent comprising:
   a hollow tube;
   a chamber having a beneficial agent therein, said chamber being mounted adjacent a first end of the hollow tube and being slidably mounted at least partially within the hollow tube from a first position to a second position, such that in the first position, the chamber extends a greater distance from the hollow tube than the second position;
   a cannula mounted within the hollow tube including a blunt end;
   means for providing fluid communication between said chamber and said cannula when said chamber is in said second position; and
   a sheath for covering at least a portion of the blunt end of the cannula including, a body member defining an interior for receiving at least a portion of the blunt cannula, the body member including a first end and a second end, the second end having an opening for receiving at least a portion of the cannula, the first end including a wall member so constructed and arranged as to rip upon the exertion of a sufficient perpendicular force by an end of the blunt cannula, and the body includes side walls extending between the first and second end, the side walls are so constructed and arranged so as to slide back along the cannula toward the second end upon the tearing of the first end by the cannula and the application of a sufficient force upon the side walls.

20. The cartridge of claim 19 including a shell circumscribing a portion of the cannula and defining a channel having an inlet and an outlet.

21. The cartridge of claim 19 wherein the body member of the sheath includes at least one seal point located on an inner surface of the body member, the seal point circumscribing a portion of the outer surface of the cannula when the cannula is received within the interior of the sheath.

22. The cartridge of claim 20 wherein the sheath includes at least one seal point that seals the inlet of the channel when the sheath is positioned over the cannula.

23. The cartridge of claim 19 wherein the wall of the first end of the sheath includes on an inner surface thereof a bevelled portion.

24. The cartridge of claim 19 wherein the wall of the first end of the sheath has a cross-sectional thickness greater than the cross-sectional thickness of a majority portion of the side walls of the sheath.

25. The cartridge of claim 19 wherein the body member of the sheath is ETO gas transmissive.

26. The cartridge of claim 19 wherein the second end of the sheath includes an annular portion that extends outwardly substantially perpendicular to the side walls.

27. A method for allowing fluid communication between a cannula including a blunt end, a portion of which is covered by a sheath, and an injection site comprising the steps of:

providing a sheath including an interior for receiving at least a portion of the blunt end of the cannula, the sheath including an end wall and side walls;

providing the cannula with a shell circumscribing an outer portion of the cannula to create a channel and causing the sheath to removably seal an inlet of the channel;

urging the end wall of sheath and blunt end of the cannula against the injection site;

causing the end wall to rip allowing the blunt end of the cannula to enter the injection site;

urging the blunt end of the cannula into the injection site; and causing the side walls to roll up away from the end wall as the cannula is received within the injection site.

28. The method of claim 27 including the step of causing the side walls to cover at least a portion of the blunt end as the cannula is removed from the injection site.

29. The method of claim 28 including the step of positioning the cannula within a cartridge for introducing a beneficial agent.

30. The method of claim 27 wherein the cannula includes a second end and including the step of establishing fluid communication between the second end of the cannula and a source of a beneficial agent.

31. The method of claim 30 including the step of establishing the fluid communication between the second end of the cannula and source prior to inserting the blunt end of the cannula into the injection site.

* * * * *